(12) United States Patent
Arino et al.

(10) Patent No.: US 12,161,741 B2
(45) Date of Patent: Dec. 10, 2024

(54) SKIN GEL PREPARATION FOR EXTERNAL USE

(71) Applicant: Shiseido Company, Ltd., Tokyo (JP)

(72) Inventors: Shoko Arino, Tokyo (JP); Yukiko Hiruma, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 996 days.

(21) Appl. No.: 17/260,821

(22) PCT Filed: Jul. 8, 2019

(86) PCT No.: PCT/JP2019/026935
§ 371 (c)(1),
(2) Date: Jan. 15, 2021

(87) PCT Pub. No.: WO2020/017371
PCT Pub. Date: Jan. 23, 2020

(65) Prior Publication Data
US 2021/0267862 A1    Sep. 2, 2021

(30) Foreign Application Priority Data

Jul. 20, 2018    (JP) ................. 2018-136912

(51) Int. Cl.
| | | |
|---|---|---|
| *A61K 31/416* | (2006.01) | |
| *A61K 8/04* | (2006.01) | |
| *A61K 8/34* | (2006.01) | |
| *A61K 8/37* | (2006.01) | |
| *A61K 8/41* | (2006.01) | |
| *A61K 8/81* | (2006.01) | |
| *A61K 8/86* | (2006.01) | |
| *A61Q 19/00* | (2006.01) | |

(52) U.S. Cl.
CPC .............. *A61K 8/416* (2013.01); *A61K 8/042* (2013.01); *A61K 8/34* (2013.01); *A61K 8/342* (2013.01); *A61K 8/375* (2013.01); *A61K 8/8147* (2013.01); *A61K 8/86* (2013.01); *A61Q 19/00* (2013.01); *A61K 2800/10* (2013.01); *A61K 2800/48* (2013.01)

(58) Field of Classification Search
CPC ...................................................... A61K 8/416
See application file for complete search history.

(56) References Cited

U.S. PATENT DOCUMENTS

| | | | |
|---|---|---|---|
| 2007/0010408 A1 | 1/2007 | Uehara | |
| 2015/0157540 A1* | 6/2015 | Rizk | ........................ A61K 8/39 510/122 |

FOREIGN PATENT DOCUMENTS

| | | |
|---|---|---|
| CN | 101217998 A | 7/2008 |
| JP | 11-181500 A | 7/1999 |
| JP | 2004-123661 A | 4/2004 |
| JP | 2013-082687 A | 5/2013 |
| JP | 2017-081876 A | 5/2017 |

OTHER PUBLICATIONS

Database GNPD [Online] Mintel; "CC Cooling Cushion SPF 42 PA ," Database Accession No. 5436639, XP055916002, Feb. 9, 2018, 6 pages.
Database GNPD [Online] Mintel; "Purifying Jelly," Database Accession No. 5616087, XP055916925, Apr. 20, 2018, 2 pages.

* cited by examiner

*Primary Examiner* — Rei Tsang Shiao
(74) *Attorney, Agent, or Firm* — Foley & Lardner LLP

(57) ABSTRACT

An objective of the present invention is to provide a gel-type skin preparation for external use into which a di-chain cationic surfactant can be stably blended without precipitation over time and which can be spread topically on skin. The gel preparation according to the present invention comprises (a) a di-chain cationic surfactant having a specific structure, (b) an oil in which component (a) is soluble, (c) a lower alcohol, (d) a water-soluble thickener, and (e) water.

11 Claims, No Drawings

SKIN GEL PREPARATION FOR EXTERNAL USE

CROSS-REFERENCE TO RELATED APPLICATIONS

This application is the U.S. National Stage of PCT/JP2019/026935, filed Jul. 8, 2019, which claims priority to JP 2018-136912, filed Jul. 20, 2018.

TECHNICAL FIELD

The present invention relates to a gel-type skin preparation for external use, in which a di-chain cationic surfactant can be stably blended and which can be easily spread topically on skin.

BACKGROUND ART

Conventionally, in the cosmetics field, cationic surfactants are known to have the effects of improving the stability, the cleaning properties, the powder dispersability and the like of preparations into which they are blended, and they are therefore used in emulsion cosmetics and the like (Patent Document 1).

Additionally, in recent years, it has been discovered that when di-chain cationic surfactants are blended in cosmetics in combination with cooling agents such as menthol, the cooling sensation effects are increased. Thus, an oil-in-water emulsion cosmetic having increased cold sensation effects and emulsion stability, in which a di-chain cationic surfactant is blended with an aqueous skin-care cosmetic has been proposed (Patent Document 2).

However, at the current time, there are no gel-type preparations that can be easily spread on a portion of the skin.

Additionally, since di-chain cationic surfactants have the problem of being difficult to dissolve in water and tending to precipitate, there is a need to deal with precipitation over time, even in the case in which a gel-type preparation is prepared.

RELATED ART

Patent Documents

Patent Document 1: JP 2007-246521 A
Patent Document 2: JP 2013-82687 A

SUMMARY OF THE INVENTION

Problem to be Solved by the Invention

An objective of the present invention is to provide a gel-type skin preparation for external use, into which a di-chain cationic surfactant can be stably blended and which can be easily spread topically on skin.

Means for Solving the Problem

As a result of diligent research towards solving the above-mentioned problem, the present inventors discovered that, by blending the di-chain cationic surfactant, a specific oil, a lower alcohol, a water-soluble thickener and water, a stable gel-type preparation in which the precipitation of the di-chain cationic surfactant is sufficiently suppressed can be obtained, thereby arriving at the present invention.

In other words, the present invention provides a skin gel preparation for external use, comprising:
(a) a di-chain cationic surfactant represented by formula (I) below:

  (I)

where $R_1$ denotes, each independently, an alkyl group having 12 to 22 carbon atoms and 0 to 3 double bonds, $R_2$ denotes, each independently, an alkyl group having 1 to 3 carbon atoms and lacking a double bond, and Y denotes a halogen atom, a methosulfate or a methophosphate;
(b) an oil in which component (a) is soluble;
(c) a lower alcohol;
(d) a water-soluble thickener; and
(e) water.

Effects of the Invention

By being configured as mentioned above, the present invention can obtain a gel-type skin preparation for external use in which a di-chain cationic surfactant is stably blended without precipitation over time. The present invention is in gel form and therefore can be easily spread topically on the face or skin. Furthermore, a di-chain cationic surfactant is stably blended in the preparation. Thus, the preparation has the effects of preventing static electricity on the skin to which it is applied, and of preventing the adhesion of air-borne fine particles.

MODES FOR CARRYING OUT THE INVENTION

The preparation according to the present invention is characterized by containing (a) a di-chain cationic surfactant having a specific structure, (b) an oil in which component (a) is soluble, (c) a lower alcohol, (d) a water-soluble thickener and (e) water. Hereinafter, the components constituting the preparation according to the present invention will be described in detail.

<(a) Di-Chain Cationic Surfactant>

As the (a) di-chain cationic surfactant (hereinafter sometimes referred to simply as "component (a)") blended in the preparation according to the present invention, the di-chain cationic surfactant represented by formula (I) below can be favorably used.

  (I)

In the above formula (I), $R_1$ denotes, each independently, an alkyl group having 12 to 22 carbon atoms and 0 to 3 double bonds, $R_2$ denotes, each independently, an alkyl group having 1 to 3 carbon atoms and lacking a double bond, and Y denotes a halogen atom, a methosulfate or a methophosphate.

Examples of the di-chain cationic surfactant represented by formula (I) above include, but are not limited to, dibehenyl dimethyl ammonium chloride, distearyl dimethyl ammonium chloride (commercially available as "Cation DSV" (manufactured by Sanyo Chemical Industries Co., Ltd.) etc.), dicetyl dimethyl ammonium chloride, dicetostearyl dimethyl ammonium chloride, distearyl dimethyl ammonium methosulfate, dibehenyl dimethyl ammonium methosulfate, dicetyl dimethyl ammonium methosulfate, dicetostearyl dimethyl ammonium methosulfate chloride and the like. Among the above, distearyl dimethyl ammonium chloride is preferably used.

The blended amount of component (a) should be 0.001% to 1% by mass, preferably 0.005% to 0.1% by mass within the total mass of the preparation. If the amount is less than 0.001% by mass, then the effects due to the di-chain cationic surfactant cannot be obtained. On the other hand, if the amount exceeds 1% by mass, then there is poor emulsion stability when stored. As component (a), it is possible to use one type alone or to use a combination of two or more types of the above-mentioned di-chain cationic surfactants.

<(b) Oil in which Component (a) is Soluble>

The (b) oil in which component (a) is soluble (hereinafter sometimes referred to simply as "component (b)") that is blended in the preparation according to the present invention is an oil that can dissolve component (a). In this case, to "dissolve component (a)" refers to an oil such that, when 1 g of the (a) di-chain cationic surfactant is mixed with and heated to dissolve in 100 g of the oil, the solution remains stable, without precipitation or clouding, even after being placed at rest for 24 hours at ambient temperature.

Component (b) in the present invention can be selected from among oils and fats, hydrocarbon oils, silicone oils, higher alcohols, synthetic ester oils, natural ester oils and the like. Of the above, it is preferably selected from among higher alcohols, ester oils having hydroxy groups, monoglycerides, diglycerides, monoalkyl glyceryl ethers, monoalkenyl glyceryl ethers, dialkyl glyceryl ethers, dialkenyl glyceryl ethers and the like.

Preferable examples of component (b) include, for example, isostearyl alcohol, octyldodecanol, diisostearyl malate, glyceryl diisostearate, ethylhexyl glycerin and the like. Of the above, it is particularly preferable to use isostearyl alcohol or octyldodecanol.

The blended amount of component (b) should be 0.01% to 10% by mass, preferably 0.1% to 5% by mass within the total mass of the preparation. If the blended amount is less than 0.01% by mass, then there are cases in which the effects due to blending the oil cannot be obtained, such as not being able to stably dissolve various types of oil-based surfactants. On the other hand, if the blended amount is more than 10% by mass, then stickiness occurs after application, which is unfavorable. As component (b), it is possible to use one type alone or to use a combination of two or more types of the above-mentioned oils.

<(c) Lower Alcohol>

The (c) lower alcohol (hereinafter sometimes referred to simply as "component (c)") blended in the preparation according to the present invention is a monohydric lower alcohol having 1 to 3 carbon atoms, which can normally be used in cosmetics. Specific examples include methanol, ethanol, n-propanol, isopropyl alcohol and the like. Component (c) contributes to an increased cooling sensation, increased storage stability, microscopic fine particle formation and the like.

The blended amount of component (c) should be 10% to 60% by mass, preferably 20% to 60% by mass, more preferably 10% to 50% by mass or 20% to 50% by mass, and even more preferably 10% to 40% by mass or 20% to 40% by mass relative to the total mass of the preparation. If the blended amount is less than 10% by mass, then the preparation becomes sticky, and if the blended amount exceeds 60% by mass, then there are cases in which component (a) cannot be stably blended.

In the preparation according to the present invention, if a higher alcohol is blended as component (b), then for the purpose of preventing the solubilization of the higher alcohol with an aqueous alcohol solution and for the purpose of preventing stickiness, the blended amount of the lower alcohol is preferably 10% to 60% by mass or 20% to 60% by mass, more preferably 10% to 50% by mass or 20% to 50% by mass, and even more preferably 10% to 40% by mass or 20% to 40% by mass.

<(d) Water-Soluble Thickener>

The (d) water-soluble thickener (hereinafter sometimes referred to simply as "component (d)") blended in the preparation according to the present invention is a water-soluble thickener that can normally be used in cosmetics. Specifically, examples include, but are not limited to, plant-based polymers such as gum arabic, tragacanth gum, galactan, guar gum, carrageenan, pectin, quinceseed (marmelo) extract, brown algae powder and agar; microbe-based polymers such as xanthan gum, dextran and pullulan; animal-based polymers such as collagen, casein, albumin and gelatin; starches such as starch, carboxymethyl starch and methylhydroxy starch; celluloses such as methylcellulose, nitrocellulose, ethylcellulose, methylhydroxypropylcellulose, hydroxyethylcellulose, cellulose sulfuric acid salts, hydroxypropylcellulose, carboxymethylcellulose, crystalline cellulose and cellulose powder; vinyl polymers such as polyvinyl alcohol, polyvinyl methyl ether, polyvinylpyrrolidone and carboxyvinyl polymers; acrylic polymers such as polyacrylic acid and salts thereof, and polyacrylimides; hydrophobically modified polyether urethanes such as acrylic acid/alkyl methacrylate copolymers, acrylates/alkyl acrylate cross-polymers and PEG-240/decyltetradeceth-20/hexamethylene diisocyanate copolymers; glycyrrhetinic acid, alginic acid and salts thereof, and the like. As component (d), it is possible to use one type alone or to use a combination of two or more types of the above. For example, it is preferable to use one or more types selected from among carboxyvinyl polymers, PEG-240/decyltetradeceth-20/hexamethylene diisocyanate copolymers and acrylates/alkyl acrylate (C10-30) cross-polymers.

Of the above, component (d) is preferably a water-soluble thickener having emulsifying properties. Specific examples that are commercially available include PEG-240/decyltetradeceth-20/hexamethylene diisocyanate copolymer (product name "Adekanol GT-200", manufactured by Adeka Corp.), acrylates/alkyl acrylate (C10-30) cross-polymer (product name "PEMULEN TR-1", manufactured by Lubrizol Advanced Materials), acrylates/steareth-20 methacrylate copolymer (product name "Aculyn", manufactured by Rohm & Haas) and the like. Additionally, in order to adjust the viscosity, a combination of a water-soluble thickener having emulsifying properties and a water-soluble thickener not having emulsifying properties may be used.

The blended amount of component (d) should be 0.1% to 5% by mass, preferably 0.3% to 2.0% by mass relative to the total mass of the preparation. If the blended amount is less than 0.1% by mass, then there are concerns about dripping from the fingers and the emulsion stability becoming worse. If the blended amount exceeds 5% by mass, then the stretchability at the time of application is poor and the texture can be degraded, which is unfavorable.

<(e) Water>

Examples of the (e) water (hereinafter sometimes referred to simply as "component (e)") blended in the preparation according to the present invention include, but are not limited to, ion-exchanged water, purified water and natural water.

The blended amount of component (e) should be 30% to 95% by mass, preferably 40% to 90% by mass relative to the total mass of the preparation.

By blending a surfactant in the preparation according to the present invention, the emulsion stability of the preparation can be further increased. The surfactant may be of one or more types selected from among non-ionic surfactants that have conventionally been used in oil-in-water emulsion cosmetics, among which non-ionic surfactants having an HLB of 8 or higher, preferably 10 or higher and more preferably 12 or higher are used. Specific examples include, but are not limited to, polyoxyethylene hardened castor oils such as PEG-10 hydrogenated castor oil, PEG-20 hydrogenated castor oil, PEG-25 hydrogenated castor oil, PEG-30 hydrogenated castor oil, PEG-40 hydrogenated castor oil, PEG-50 hydrogenated castor oil, PEG-60 hydrogenated castor oil, PEG-80 hydrogenated castor oil and PEG-100 hydrogenated castor oil.

However, in the case in which a surfactant is blended in the preparation according to the present invention, in order to suppress stickiness of the preparation, the blended amount of the surfactants other than component (a) should preferably be 1% by mass or less relative to the total amount of the preparation.

<Other Blendable Components>

Aside from the above-mentioned components, the preparation according to the present invention may further contain, appropriately as needed, within a range not compromising the effects of the present invention, other components that are normally used in cosmetics such as, for example, water-soluble polymers, powder components, ultraviolet protectants, various types of aqueous solvents, oil-soluble agents, essential oils, moisturizers, antioxidants, metal sequestrants, pH adjusters, fragrances, preservatives and the like.

The di-chain cationic surfactant that is an essential component in the present invention has antistatic effects, and thus has been conventionally used by being blended into compositions for the purpose of being applied to clothes to remove static electricity. In the cosmetics field, a hair-care cosmetic having excellent hairstyling properties, in which a di-chain cationic surfactant is blended to suppress static electricity, has been proposed (Patent Document 3: JP 2010-163384 A). In cosmetics as well, if a gel-type preparation containing a di-chain cationic surfactant could be obtained, then static electricity could be removed from the areas to which the preparation has been applied. Additionally, such gel preparations can, by removing static electricity, suppress the adhesion to skin of harmful matter that is suspended in air, such as pollen, viruses and PM2.5.

With the preparation according to the present invention, a di-chain cationic surfactant can be stably blended and the preparation can be used by being applied to skin. Thus, a gel-type cosmetic having antistatic effects can be provided. Since the cosmetic has antistatic effects, it can prevent the adhesion of air-borne fine particles to skin on which the cosmetic has been applied. The cosmetic according to the present invention is a novel gel-type cosmetic in that it has the function of preventing the adhesion of air-borne fine particles to skin.

In the preparation according to the present invention, the blended amount of the surfactants other than component (a) is preferably 1% by mass or less in order to suppress the stickiness of the preparation. By suppressing the stickiness of the preparation itself, the fine particle adhesion prevention effects due to the antistatic effects of the (a) di-chain cationic surfactant are maximized.

The viscosity of the preparation according to the present invention is appropriately adjusted in accordance with the embodiment and is, for example, 5,000 to 100,000 mPa·s. The viscosity in this case refers to the viscosity (mPa·s) as measured by means of a BH-type viscometer (rotor no. 6, 10 rotations, 1 minute) after the prepared sample has been placed at rest for 1 day at 30° C.

Additionally, in the preparation according to the present invention, the average emulsion particle should preferably have a size of 0.1 to 20 μm for the purpose of emulsion stability.

Additionally, in the preparation according to the present invention, a substance having static electricity removal effects, such as a 2-(meth)acryloyloxyalkyl phosphorylcholine/(meth)acrylic acid alkyl ester copolymer, may be further blended in addition to component (a) in the present application for the purpose of increasing the air-borne fine particle adhesion prevention effects.

The preparation according to the present invention may be prepared in the form of a transparent gel or in the form of a cloudy gel. The preparation according to the present invention is in the form of a gel, and thus has the convenience of being easy to spread on a desired skin surface. Additionally, for example, when providing a cosmetic for preventing the adhesion of air-borne fine particles such as pollen, the fine particle adhesion prevention function is particularly effective due to the cosmetic being in the form of a gel that can be partially applied around the eyes, the nose and the mouth.

The preparation according to the present invention lacks stickiness, has a suitable viscosity, and has an excellent texture. For this reason, the preparation according to the present invention can be applied to a wide range of cosmetics, and can be provided in any form including, for example, a milky lotion, an essence, a cream, a sunscreen cosmetic, a makeup base, a foundation, a lip rouge, a blush, an eyeshadow and the like.

The preparation according to the present invention can be manufactured by a conventional method. As an example, it may be prepared by separately stirring and mixing the water phase components and the oil phase components to prepare a water phase portion and an oil phase portion that are homogeneous, then stirring and mixing the water phase portion while adding the oil phase portion thereto.

EXAMPLES

Hereinafter, the present invention will be explained in further detail by providing examples. However, the present invention is not limited to these examples in any way. Where not otherwise noted, the blended amounts are indicated in percentage by mass relative to the system in which the component is blended.

Before performing the examples, the solubility of the (a) di-chain cationic surfactant according to the present invention in oils was tested by the method described below.

After mixing and heating to dissolve 1 g of distearyldimonium chloride in 100 g of each of the oils indicated in Table 1 below and placing the solutions at rest for 24 hours at ambient temperature, the states thereof were observed. The evaluation results are also shown in Table 1. The oils that remained homogeneously transparent are indicated by a "○", and those that were cloudy or precipitated are indicated by a "x".

TABLE 1

| Oil | Evaluation Result |
| --- | --- |
| Cyclomethicone | x |
| Diphenylsiloxy phenyl trimethicone | x |
| Mineral oil | x |
| Vegetable squalane | x |
| Cetyl ethylhexanoate | x |
| Triethylhexanoin | x |

TABLE 1-continued

| Oil | Evaluation Result |
|---|---|
| Pentaerythrityl tetraethylhexanoate | x |
| Isododecane | x |
| Hydrogenated polyisobutene | x |
| Jojoba oil | x |
| Neopentyl glycol dicaprate | x |
| Triisostearin | x |
| Diisostearyl malate | ○ |
| PPG-3 dipivalate | x |
| 2-Ethylhexyl succinate | x |
| Macadamia nut oil | x |
| Ethylhexylglycerin | ○ |
| Isostearyl alcohol | ○ |
| Isostearic acid | x |
| Octyldodecanol | ○ |
| Triisostearin | x |
| Glyceryl diisostearate | ○ |
| Di(phytosteryl/octyldodecyl) lauroyl glutamate | x |

As shown in Table 1, the di-chain cationic surfactant according to the present invention homogeneously dissolved in isostearyl alcohol, octyldodecanol, diisostearyl malate, glyceryl diisostearate and ethylhexylglycerin.

Examples 1 to 6

Gel preparations having the compositions indicated in Table 2 below were prepared in accordance with conventional methods, and the emulsion stabilities thereof were investigated in accordance with the evaluation method described below. The evaluation results are also shown in Table 2.

(1) Viscosity

After placing the prepared samples at rest for 1 day at 30° C., the viscosities (mPa·s) thereof were measured with a BH-type viscometer (rotor no. 6, 10 rotations, 1 minute). The preparation according to the present invention preferably has a viscosity of 5,000 to 100,000 mPa·s.

(2) Average Emulsion Particle Size

The emulsion particle sizes of droplets after sample preparation were measured by using a microscope. As the average emulsion particle size becomes smaller, the emulsion stability becomes better, and if the size exceeds 10 μm, then there is a higher tendency for separation to be observed upon long-term storage. In the preparation according to the present invention, the average emulsion particle size is preferably 0.1 to 20 μm.

(3) Presence or Absence of Precipitation

After placing prepared samples at rest for 7 days at 0° C. and 25° C., the presence or absence of precipitation of the blended components was evaluated by eye or by microscope.

TABLE 2

| | Component | Ex. 1 | Ex. 2 | Ex. 3 | Ex. 4 | Ex. 5 | Ex. 6 |
|---|---|---|---|---|---|---|---|
| | Distearyl dimethyl ammonium chloride | 0.01 | 0.01 | 0.01 | 0.01 | 0.01 | 0.01 |
| | Isostearyl alcohol | 1 | 1 | 0.9 | 1.1 | 1 | 1 |
| | Ethanol | 30 | 30 | 30 | 30 | 30 | 30 |
| | PEG-240/decyltetradeceth-20/HDI) copolymer | 0.5 | 0.5 | 0.5 | 0.5 | 0.5 | 0.5 |
| | Carboxyvinyl polymer | 0.45 | 0.45 | 0.45 | 0.45 | 0.45 | 0.45 |
| | (Acrylates/alkyl acrylate (C10-30)) cross-polymer | 0.05 | 0.05 | 0.05 | 0.05 | 0.05 | 0.05 |
| | Water | bal | bal | bal | bal | bal | bal |
| | Polyquaternium-51 | 0.1 | 0.1 | 0.1 | 0.1 | 0.1 | 0.1 |
| | Orange oil | 0.03 | — | — | — | — | — |
| | Peppermint oil | 0.007 | 0.007 | 0.007 | 0.007 | 0.007 | 0.007 |
| | Rosemary leaf oil | 0.0032 | 0.0032 | 0.0032 | 0.0032 | 0.0032 | 0.0032 |
| | Sage oil | 0.002 | 0.002 | 0.002 | 0.002 | 0.002 | 0.002 |
| | Eucalyptus oil | 0.003 | 0.003 | 0.003 | 0.003 | 0.003 | 0.003 |
| | Menthol | — | 0.12 | 0.12 | 0.12 | 0.12 | 0.12 |
| | PEG-60 hydrogenated castor oil | — | — | — | — | 0.01 | 0.1 |
| | 2-amino-2-methyl-1,3-propanediol | 0.4 | 0.4 | 0.4 | 0.4 | 0.4 | 0.4 |
| | Fragrance | 0.1 | — | — | — | — | — |
| | Total | 100 | 100 | 100 | 100 | 100 | 100 |
| Evaluation | (1) Viscosity (mPa · s) | 62800 | 62400 | 68800 | 60200 | 63400 | 63400 |
| | (2) Average emulsion particle size (μm) | 1 | 1 | 1 | 1 | 1 | 1 |
| | (3) Precipitation | none | none | none | none | none | none |

As shown in Table 2, in all of the examples containing components (a) to (e) of the present invention, precipitation of the di-chain cationic surfactant did not occur, and gel preparations having excellent emulsion stability and suitable viscosity were able to be obtained.

The invention claimed is:

1. A skin gel preparation for external use, comprising:
   (a) a di-chain cationic surfactant represented by formula (I) below:

$$[(R_2)_2-N^+-(R_1)_2]Y^- \quad (I)$$

where $R_1$ denotes, each independently, an alkyl group having 12 to 22 carbon atoms and 0 to 3 double bonds, $R_2$ denotes, each independently, an alkyl group having 1 to 3 carbon atoms and lacking a double bond, and Y denotes a halogen atom, a methosulfate or a methophosphate;
   (b) an oil in which component (a) is soluble;
   (c) a lower alcohol;
   (d) a water-soluble thickener; and
   (e) water.

2. The skin gel preparation for external use as in claim 1, wherein a blended amount of a surfactant other than component (a) is 1% by mass or less.

3. The skin gel preparation for external use as in claim 1, wherein component (a) is distearyl dimethyl ammonium chloride.

4. The skin gel preparation for external use as in claim 1, wherein component (b) is of one or more types selected from the group consisting of higher alcohols, ester oils having hydroxy groups, monoglycerides, diglycerides, monoalkyl glyceryl ethers, monoalkenyl glyceryl ethers, dialkyl glyceryl ethers and dialkenyl glyceryl ethers.

5. The skin gel preparation for external use as in claim 1, wherein, if component (b) is a higher alcohol, then a blended amount of the (c) lower alcohol is 10% to 60% by mass.

6. The skin gel preparation for external use as in claim 1, wherein the (d) water-soluble thickener is of one or more types selected from among a carboxyvinyl polymer, a PEG-240/decyltetradeceth-20/hexamethylene diisocyanate copolymer and an acrylates/alkyl acrylate (C10-30) cross-polymer.

7. The skin gel preparation for external use as in claim 1, for use by application with a finger or the like.

8. The skin gel preparation for external use as in claim 1, wherein a blended amount of said (a) is 0.001% to 1% by mass, a blended amount of said (b) is 0.01% to 10% by mass, a blended amount of said (c) is 10% to 60% by mass, a blended amount of said (d) is 0.1% to 5% by mass, and a blended amount of said (e) is 30% to 95% by mass.

9. The skin gel preparation for external use as in claim 1, wherein the component (b) is of one or more types selected from the group consisting of isostearyl alcohol, octyldodecanol, diisostearyl malate, glyceryl diisostearate, ethylhexyl glycerin.

10. The skin gel preparation for external use as in claim 1, wherein the component (d) is of one or more types selected from the group consisting of gum arabic, tragacanth gum, galactan, guar gum, carrageenan, pectin, quinceseed (marmelo) extract, brown algae powder, agar; xanthan gum, dextran, pullulan; collagen, casein, albumin, gelatin; starch, carboxymethyl starch, methylhydroxy starch; methylcellulose, nitrocellulose, ethylcellulose, methylhydroxypropylcellulose, hydroxyethylcellulose, cellulose sulfuric acid salts, hydroxypropylcellulose, carboxymethylcellulose, crystalline cellulose, cellulose powder; polyvinyl alcohol, polyvinyl methyl ether, polyvinylpyrrolidone, carboxyvinyl polymers; polyacrylic acid and salts thereof, polyacrylimides; acrylic acid/alkyl methacrylate copolymers, acrylates/alkyl acrylate cross-polymers, PEG-240/decyltetradeceth-20/hexamethylene diisocyanate copolymers; glycyrrhetinic acid and salts thereof, and alginic acid and salts thereof.

11. A method preventing adhesion of fine particles, the method comprising applying the skin gel preparation for external use as in claim 1 to a skin of a subject in need thereof, wherein said applying prevents adhesion of fine particles to the skin of the subject.

* * * * *